United States Patent [19]

Alzner

[11] Patent Number: 5,458,935
[45] Date of Patent: Oct. 17, 1995

[54] THERMOPLASTIC URETHANE ELASTOMER

[75] Inventor: Bernard G. Alzner, Round Lake, Ill.

[73] Assignee: Abbott Laboratories, Abbott Park, Ill.

[21] Appl. No.: 135,366

[22] Filed: Oct. 12, 1993

Related U.S. Application Data

[63] Continuation of Ser. No. 814,365, Dec. 24, 1991, abandoned.

[51] Int. Cl.$^6$ .................................................. A61M 25/00
[52] U.S. Cl. ................... 428/35.7; 428/36.8; 428/36.92; 264/209.1; 604/280; 525/458
[58] Field of Search ............................ 525/458; 428/35.7, 428/36.8, 36.92; 264/209.1; 604/280

[56] References Cited

U.S. PATENT DOCUMENTS

| | | | |
|---|---|---|---|
| 4,026,933 | 5/1977 | Edwards et al. | 524/571 |
| 4,073,755 | 2/1978 | Berg et al. | 524/188 |
| 4,129,611 | 12/1978 | Heiss | 525/458 |
| 4,138,375 | 2/1979 | Berg et al. | 524/445 |
| 4,283,447 | 8/1981 | Flynn | 428/36.9 |
| 4,581,390 | 4/1986 | Flynn | 428/36.92 |
| 4,795,763 | 1/1989 | Gluck et al. | 521/99 |
| 5,149,722 | 9/1992 | Soukup | 521/99 |
| 5,192,607 | 3/1993 | Soukup | 521/99 |
| 5,254,618 | 10/1993 | Ohashi et al. | 524/495 |
| 5,281,677 | 1/1994 | Onwunaka et al. | 525/458 |
| 5,322,874 | 6/1994 | Fujii et al. | 524/495 |

*Primary Examiner*—Melvyn I. Marquis
*Assistant Examiner*—R. F. Johnson
*Attorney, Agent, or Firm*—A. Nicholas Trausch

[57] ABSTRACT

The invention provides a thermoplastic polyurethane elastomer which contains a blend of polyurethane resins and is suitable for use in the form of tubing. The blend has a tensile strength of more than 7000 psi and an ultimate elongation greater than 200%. The blend contains about 50% to about 80% by weight of an elastomeric polyurethane resin having a hardness in the range of about 60 to 70 Shore D units. The blend additionally contains about 20% to about 50% of a relatively rigid polyurethane resin having a hardness of about 10 units more than the elastomeric resin. The invention also provides methods for using and methods for manufacturing tubing fabricated from the thermoplastic polyurethane elastomer. Preferred extrusion conditions are described.

14 Claims, 3 Drawing Sheets

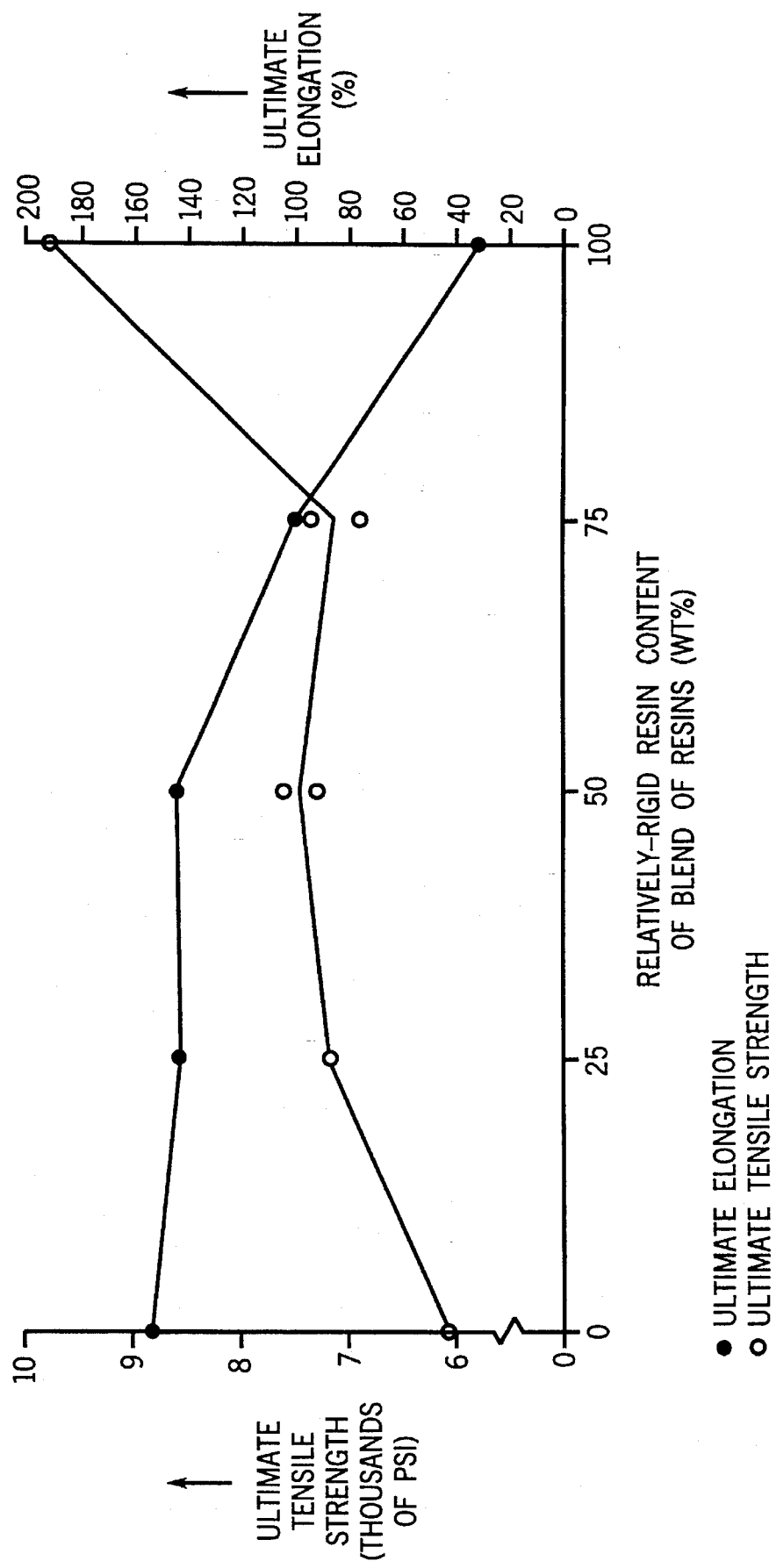

5,458,935

THERMOPLASTIC URETHANE ELASTOMER

This application is a continuation of application Ser. No. 07/814,365, filed Dec. 24, 1991, now abandoned.

TECHNICAL FIELD

The invention relates to a thermoplastic polyurethane elastomer which includes a blend of polyurethane resins that is suitable for use in tubing. Methods for using the tubing and methods for manufacturing the tubing are provided.

BACKGROUND OF THE INVENTION

No single material is suitable for all medical tubing because the specific requirements of medical applications vary greatly. It is often necessary to determine the requirements for each type of medical application and then develop a suitable material with appropriate properties. The main requirements for applications involving medical tubing are that the tubing exhibits chemical stability while in contact with body tissues and fluids, provokes little or no reaction by the patients body, and retains a capacity to deliver fluid flow when folded into tight bends. Physical properties such as strength, flexibility, hardness, and elasticity determine whether tubing is capable of delivering flow in specific conditions.

Medical tubing is used for a variety of applications, including drains, catheters, cannula, shunts, and replacements for natural tubular organs. Some of these devices are intended to remain in contact with or within the body for long periods. Others are used only briefly. Materials frequently used for medical tubing are polyethylene, polypropylene, polytetrafluoroethylene, polyvinylchloride, polydimethylsiloxane, polyurethane, and natural rubber.

Thermoplastic polyurethane elastomers are a special class of polyurethanes that soften or melt at elevated temperatures. When cooled, they recover their former physical and chemical properties. Thermoplastic polyurethane elastomers can be produced by the reaction of 4,4'-diphenylmethane diisocyanate (commonly called MDI), polyester or polyether polyols, and glycol extenders. Desired properties, such as tensile strength, elongation, and hardness, are obtained by adjusting the nature and the amount of the components, the length of polyurethane chains present in the elastomer, and the degree of cross-linking between such chains.

Representative of the thermoplastic urethane class of elastomers are the Estane™ elastomers manufactured by the B. F. Goodrich hemical Company and the Pellethane™ elastomers manufactured by the Dow Chemical Corporation. They are prepared from di- or polyisocyanates, such as MDI; glycols, polyols or multifunctional carboxylic acids, such as adipic acid; and 1,4-butanediols. Thermoplastic-thermosetting urethane polymers, such as the Texin™ polymers manufactured by Mobay Chemical Company, which may be extruded and injection molded, are Considered thermoplastic urethane elastomers. They are prepared from hydroxyl terminated polyethers, polyesters, MDI, or similar diisocyanates. The Pelletnane™ elastomers manufactured by the Dow Chemical Corporation are also classified as thermoplastic polyurethane elastomers.

While polyurethane elastomers have been utilized to manufacture medical tubing, it appears that none of the previously known tubing compositions possessed all of the physical properties which physicians seek in medical tubing. A good tubing should possess a relatively high degree of hardness, as it must often be guided through small passages to reach a location in the body where it can be put to use. It should also have a high degree of tensile strength, as mechanical failure during withdrawal of the medical tubing might cause serious complications.

At the same time, the ideal medical tubing has a sufficient degree of flexibility and elasticity, so as to conform to a patient's movements and cause no injury to the patient. Because the patient's movements tend to constrict or fold the medical tubing, it is important that the tubing continue to function as a conduit and maintain flow even while subject to external mechanical forces. Finally, when mechanical force is removed the tubing should substantially recover its original shape.

SUMMARY OF THE INVENTION

The present invention provides a composition having desirable tensile strength, ultimate elongation, hardness, and recovery characteristics. The invention also provides a medical tubing fashioned from the composition, and provides methods for the use and manufacture of the tubing.

The present invention provides a composition which includes a blend of resins. The composition is capable of being stretched to an ultimate elongation before fracture of greater than about 200%.

The blend of resins comprises an elastomeric polyurethane resin and a relatively rigid polyurethane resin. The elastomeric resin is present in an amount of from about 50% to about 80% by weight of the blend and has a hardness in the range of about 60 to about 70 Shore D units. The relatively rigid resin accounts for about 20% to about 50% by weight of the blend and has a hardness which is about 10 Shore D units greater than the hardness of the elastomeric resin. The combination of mechanical properties exhibited by the composition makes it suitable for use in medical tubing, especially as a spinal catheter.

In one aspect of the invention, the elastomeric resin and the relatively rigid resin possess significantly different ultimate elongation values. The elastomeric resin has an ultimate elongation of more than about 200% while the relatively rigid resin has an ultimate elongation of less than about 50%, based upon the length of a resin sample measured before stress was applied.

In another form, the invention provides tubing suitable for use as medical tubing. The dimensions of the tubing and the composition of which it is formed tend to enable the tubing to continue to deliver flow even when folded in a tight bend. The tubing composition comprises a blend of resins exhibiting a tensile strength of more than about 7000 psi. and an ultimate elongation of greater than about 100%. The blend of resins comprises an elastomeric polyurethane resin and a relatively rigid polyurethane resin. The elastomeric resin has a hardness of about 60 to about 70 Shore D units and is present in an amount of from about 50% to about 80% by weight, based on the blend of resins. The relatively rigid resin has a hardness of about 10 Shore D units greater than that of the elastomeric resin.

A particular embodiment of the invention is a tubing having a passage for flow within. The tubing can be folded into a tight 180 degree bend, pinched so that the passage for flow is blocked, released, and thereafter exhibits a residual angle of only about 45 degrees or less.

Another embodiment of the invention is a tubing which can be folded into a tight 90 degree bend and remains capable of passing about 85% or more of the flow that is passed by a straight tube of equal dimensions under similar hydraulic conditions.

The invention also provides a method for injecting a therapeutic fluid into a human body. The method comprises providing a tube member which is formed of a blend of resins of the present invention. The blend of resins exhibits an ultimate elongation of more than about 200% and a tensile strength of more than about 7000 psi. The blend of resins comprises an elastomeric polyurethane resin with a hardness in the range of about 60 to 70 Shore D units and also a relatively rigid polyurethane resin having a hardness of about 10 Shore D units greater than that of the elastomeric resin. The elastomeric resin constitutes about 50% to about 80% by weight of the blend of resins. The relatively rigid polyurethane resin constitutes about 20% to about 50% by weight of the blend.

The method for injecting a therapeutic fluid also comprises the step of inserting the tube into the human body. For example, the insertion could be epidural, intravenous, or into an existing body cavity. The tubing may be completely inserted into the body or may protrude through the skin. The therapeutic fluid is passed through the tube member and into the body.

Alternatively, the tube member so provided and inserted into the body can be used for drawing a sample of body fluids or as a conduit for measuring the pressure of fluids contained within the body.

The invention also provides a method of manufacturing tubing that comprises mixing two polyurethane resins having different hardness values. An elastomeric polyurethane resin having a hardness in the range of about 60 to 70 Shore D units is mixed with a relatively rigid polyurethane resin having a hardness which is about 10 Shore D units greater than that of the elastomeric resin. A mixture of resins is produced which contains about 20% to about 50% by weight of the relatively rigid resin and about 50% to about 80% by weight of the elastomeric resin. The mixing may be carried out using powdered or pelletized dry resins or performed in hot-melt fashion.

The method of manufacturing also comprises fusing the mixture of resins to produce a blend of resins. When cooled to room temperature, the blend of resins has a tensile strength f more than about 7000 psi. and an ultimate elongation of greater than about 0 200%, based upon the length of a test sample measured before stress is applied.

The blend of resins is extruded to produce the tubing. Extruding is performed at an elevated temperature using thermoplastic polyurethane resins. It is preferred that the blend of resins is extruded from a die having an average diameter of about 2 to about 10 times the average diameter of the final tubing. This ratio is commonly called the diameter draw ratio and has been found to significantly affect physical properties of the finished tubing.

Similarly, extruding the blend of resins may, optionally, be accomplished using a die having a wall gap which is in the range of about 2.0 to about 10.0 times the wall thickness of the finished tubing range of about 4.0 to about 6.0. The wall gap is the thickness of the opening in an extrusion die through which a tubing wall issues. The wall gap-to-wall thickness ratio is commonly called a wall draw ratio.

In yet another aspect of the invention, the blend of resins is cooled after fusing to produce a solid intermediate product. The intermediate product may be stored or transported before further processing into tubing.

The invention also provides a method of manufacturing short tube sections by injection molding. Short tube sections are lengths of tubing having an overall length in the range of about 1.0 to about 2.0 inches. The internal bore diameters of short tube sections are often controlled to exacting tolerances. The method comprises mixing an elastomeric polyurethane resin and a relatively rigid polyurethane resin as described above to produce a mixture of resins. The mixture of resins is fused to produce a blend of resins. The blend of resins is injection molded to produce the short tube sections.

BRIEF DESCRIPTION OF THE DRAWINGS

FIG. 1 illustrates the change in ultimate elongation and ultimate tensile strength properties of polyurethane compositions as the percentage of relatively rigid resin varies.

DESCRIPTION OF THE PREFERRED EMBODIMENTS

Figure 2A:
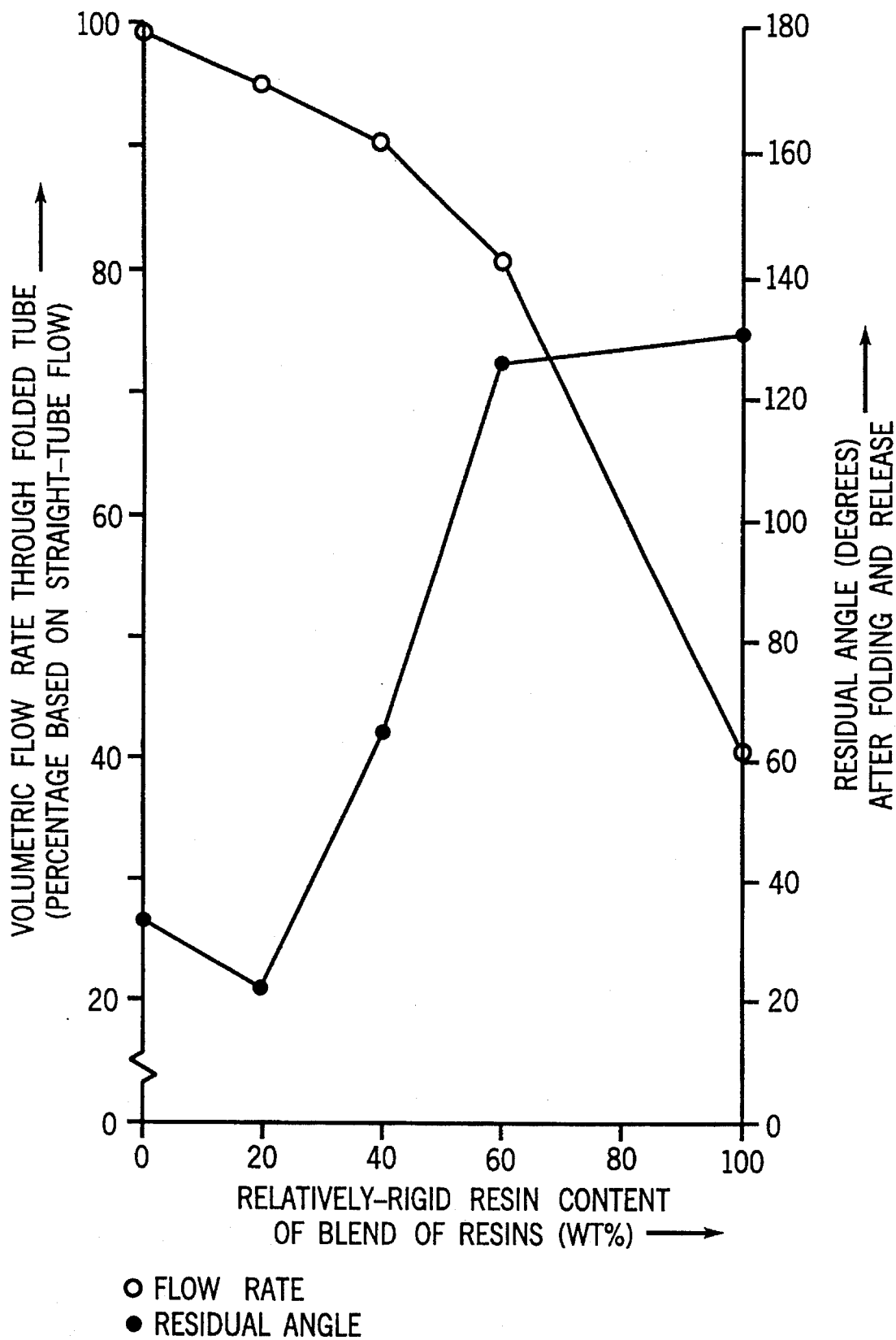
FIG. 2A illustrates change in volumetric flow rate (through tubing bent 180 degrees) and residual angle (after 180 degree bend) of tubing made from polyurethane compositions as the percentage of relatively rigid resin varies.

The composition of the present invention exhibits a combination of physical properties which is especially suitable for forming medical tubing. Tubing constructed of the composition is hard, strong, and elastic. The tubing continues to pass a significant volumetric flow even when folded into tight bends and tends to recover from deformation when released from mechanical stress.

The composition of the present invention comprises a blend of resins. The blend contains at least two resins which are macromolecular polymers of synthetic origin. The resins have been thoroughly mixed in a liquid state so as to produce a substantially homogenous solid phase. When the blend of resins is thermoplastic, the resins are conveniently mixed by fusing the resins to produce the liquid state. The blend may additionally comprise other resins and other components, as long as the chemical and physical properties of the blend are not significantly changed by their presence.

The blend of resins has a tensile strength of more than about 7000 psi. The blend may have a tensile strength of 10,000 psi or more. "Tensile strength", as the term is used here, means tensile stress at breakage determined according to American Society for Testing and Materials (ASTM) Test Method No. D412. The tensile strength of the blend may be varied according to the nature and the proportion of individual resins utilized in preparing the blend.

The blend exhibits an ultimate elongation that is greater than about 200%, preferably greater than about 300%. Ultimate elongation is also determined by ASTM Test Method No. D412. Elongation refers to a change in length of a test sample observed as tensile stress is applied. The change in length of the sample is reported as a percentage of the original length of the sample.

Ultimate elongation is measured at the point where breakage of the sample occurs. It is a useful indicator of the elasticity and flexibility which a tubing made from a particular composition will exhibit during use. Ultimate elongation may be varied by varying the nature and proportion of resins used in the blends, and also by curing the blend of resins promote increased cross-linking between polyurethane chains. Such curing can take place before or after the blend of resins is formed into a product.

The resins present in the blend of resins are polyurethane resins. Polyurethane resins can be prepared by polymerizing di- or triisocyanates with diols or triols. Generally, polyurethanes having longer backbone chains exhibit higher tensile strength. Those with a greater degree of cross-linking between the chains exhibit greater rigidity and hardness.

The polyurethane resins of the present invention are present in the form of elastomers rather than flexible foams or rigid foams. An elastomer is an elastic, rubberlike substance having a hardness of up to about 75 Shore D units, as determined by ASTM Test Method No. 2.240. The distinguishing characteristic of an elastomer is its ability to recover an original shape after being deformed and released. Generally, resins which have greater tensile strength and greater hardness are less elastomeric.

Polyurethane resins of the present invention are based upon polyethers rather than polyesters. Because the composition is intended to be suitable for use in medical tubing, the composition must be substantially chemically inert while in contact with body tissues and fluids for a time period commensurate with a particular medical application. Polyurethanes which are based upon esters, are generally tougher than those based upon polyethers, but tend to hydrolyze and degrade when exposed to water.

Accordingly, the polyurethanes which are based upon polyethers usually exhibit superior resistance to hydration and are, therefore, more suitable for use in medical tubing. The polyurethanes utilized in the present invention are aromatic/polyethers. Of course, other components such as stabilizers or radiopaque agents may also be present in the blend of resins.

Polyurethane resins which are suitable for use as the elastomeric resin in the present invention include millable gums based upon polyethers, such as the Adiprene™ resins produced by DuPont de Nemours & Company. Also suitable, are the thermoplastic-thermosetting polymers provided by Mobay Chemical Company under the name of Texin™. Excellent results have been obtained by employing Pellethane™ resin which is manufactured by the Dow Chemical Corporation as the elastomeric resin. The Pellethane™ resins, which are preferred, are polymers prepared by reacting polytetramethylene glycol ether and 4,4'-methylene diphenyldiisocyanate.

Also present in the composition is a relatively rigid polyurethane resin. The relatively rigid resin may be of the same nature as the elastomeric resin, as for example, two different grades of Pellethane™ resin included in the same composition. Alternatively, the elastomeric resin and the relatively rigid resin may have significantly different chemical and physical properties.

The relatively rigid resin may have a hardness in the elastomeric range or it may Nave a greater hardness. That is, the relatively rigid resin may have a hardness which is greater or less than about 75 Shore D hardness units. However, the relatively rigid polyurethane resin must have a hardness that is about 10 Shore D units greater than the hardness of the elastomeric resin.

Resin blends having various combinations of tensile strength and hardness are known. Generally, increases in resin tensile strength and hardness come at the expense of ultimate elongation. The trend in polyurethane compositions, although not entirely predictable, is for ultimate elongation-to decrease when tensile strength is increased at constant hardness. Surprisingly, within certain ranges a blend of resins containing an elastomeric polyurethane resin and a relatively rigid polyurethane resin exhibits simultaneous increases in tensile strength, ultimate elongation, and yield point as the hardness of the blend is increased by varying the proportion of the relatively rigid polyurethane resin.

More specifically, it has been found that a blend of resins comprising from about 50% to about 80% of an elastomeric resin, having a hardness in the range of about 60 to 70 Shore D units, exhibits increased ultimate elongation, tensile strength, and yield point, as compared to the elastomeric resin alone, when from about 20% to about 50% by weight of a relatively rigid polyurethane resin having a hardness of about 10 Shore D units greater than the elastomeric resin is present in the blend.

Rigid polymers usually possess greater strength than elastomeric polymers but do not recover their original shape when strained beyond a certain point. Elastomers recover from such strains, if not stretched to breaking, but generally possess relatively poor strength and hardness. However, blends containing approximately 10% to 50%, preferably 15% to 40%, of a rigid polyurethane resin and a elastomeric polyurethane resin possess relatively high strength, high ultimate elongation, and superior strain recovery properties that are not found in the constituent materials.

It was found that optimum kink recovery qualities are exhibited by compositions comprising in the range of about 0 to about 25% by weight, but no more than approximately 50%, of a relatively rigid polyurethane resin in an elastomeric polyurethane resin matrix. The composition of the present invention is unique in that it combines measurable rigidity, hardness, and strength properties with strain recovering properties that are not possessed by the constituent materials.

The following examples illustrate the present invention.

EXAMPLE 1

Equal parts by weight of two grades of commercially available polyurethane resin pellets were dry mixed. One of the grades was Pellethane 2363-65D produced by the Dow Chemical Corporation. It is a thermoplastic polyurethane resin having a nominal hardness of 65 Shore D units. The other grade was Pellethane 2363-75D with a nominal hardness of 75 Shore D units. Mixtures were prepared having 0%, 25%, 50%, 75% and 100% of the Pellethane™ 75D pellets, with the balance being 65D pellets.

The mixtures so produced were individually fused to produce several blends of resins. The blends were extruded through a die having a 6:0–1:0 diameter draw ratio to produce extrudate samples. The extrudate samples were tested for tensile strength, ultimate elongation, and yield point.

The results of the strength and elongation testing are disclosed graphically in FIG. 1. No measurable yield region could be discerned for the extrudate sample containing 0% of the 75D hardness resin. Yield points were measurable and increased with increasing proportion of the 75D hardness resin for all of the other samples.

Referring now to FIG. 1, it is apparent that the ultimate elongation decreases with increasing content of the 75D hardness resin except in the region from 25% to 50% where elongation remains constant or, perhaps, slightly increases. Also, the tensile strength as a function of the content of the harder resin passes through a maximum at approximately 50% of the 75D resin and decreases in the region from 50% to 75%. Surprisingly, the region between about 25% and about 50% of the 75D resin exhibits both a measurable yield point and a tensile strength which is high and increases as a function of 75D hardness, while the ultimate elongation is relatively insensitive to 75D resin content. The compositions having from about 25% to about 50% Pellethane™ 2363-75D, with the balance being Pellethane with 65D hardness, display an unusual and useful combination of properties.

Preferably, the elastomeric resin has an ultimate elongation of more than 100% and the relatively rigid resin has an ultimate elongation of less than about 50%. The inclusion of resins having significantly different physical properties is believed to give rise to important anomalies in the physical properties of the blend of resins.

In another form, the invention provides tubing suitable for use as a catheter. The tubing is formed from a composition of the type disclosed above. The blend of resins is preferably a thermoplastic elastomer. Such thermoplastic elastomers can be conveniently extruded and injection molded to produce tubing.

The invention can provide tubing which exhibits a residual angle of about 45° or less after being folded into a tight 180° bend, pinched, and released. "Residual angle" is defined as the deviation in degrees from a linear configuration of a test length of tubing which has been tightly folded and released. Most conventional tubing becomes kinked when forced into a tight 180° bend and pinched, the flow through such tubing is substantially restricted. After being released most conventional tubing does not spring back to a shape approximating a straight line, as does the tubing of the present invention, but rather retains a recovered angle which does not approach 180°. Tubing which demonstrates low residual angle is more likely to recover from deformations which are routinely encountered in medical applications and is, therefore, more likely to be suitable as a catheter.

Another aspect of the invention provides tubing which when folded into a 90° bend remains capable of passing about 85% or more of the flow that could be passed by a straight tube of equal dimensions under similar hydraulic flow conditions. It is believed that the combination of physical properties displayed by the composition described above makes the tubing of the present invention relatively resistant to substantial flow restrictions which are often observed in conventional tubing. Experiments were performed with tubing of the present invention which demonstrate a small residual angle and a capacity to continue delivering flow even when tightly folded. These experiments are summarized below as EXAMPLE 2.

EXAMPLE 2

Tubing was formed from the extrudate samples whose manufacture was described above in EXAMPLE 1. While test lengths of the tubing were disposed in an approximately straight path between known inlet and outlet hydraulic conditions, volumetric flow rates were measured and recorded. Then the test lengths were folded into tight 180° bends and pinched, while the volumetric flow rates were measured again, maintaining the same inlet and outlet hydraulic flow conditions. The flow test procedure was performed upon lengths of tubing fashioned from extrudate samples having 0%, 20%, 40%, 60% and 100% of the 75D hardness resin, with the balance being 65D hardness resin. The results of the flow testing can be seen in FIG. 2A. The flow rates observed while the test lengths were folded are expressed as a percentage of the volumetric flow rates which were measured and recorded while the same test lengths of tubing were disposed in straight paths.

Samples of each composition of tubing were also tested for residual angle. First, straight lengths of tubing which had not experienced any bending were selected. Then, each length was folded into a tight 180° bend, held motionless for a predetermined period of time, and released. The number of degrees which each released length of tubing fell short of returning to the original straight angle configuration is recorded on the right hand axis of the graph depicted in FIG. 2A.

Referring now to FIG. 2A, the test length formed of a composition which comprised only 65D hardness resin continued to pass 98% of straight tube flow while folded into a tight 180° bend and pinched. As the proportion of 75D hardness resin in the tubing was increased, the volumetric flow exhibited in the folded state decreased slightly and proportionately in the range of 0% to about 40% 75D resin content.

However, the decrease in volumetric flow rate observed for folded test lengths of tubing was much larger at 40% 75D resin content. The flow observed for a folded test length of tubing formed entirely of 75D hardness resin was only 60% of the flow observed when the same test length was held straight. Therefore, it can be concluded that tubing having less than about 50% 75D resin content with the balance being 65D hardness resin demonstrates a surprising advantage for passing flow while disposed in a tightly folded configuration.

Similarly, the results for residual angle testing, as communicated in FIG. 2A, indicate that all of the residual angles measured for tubing having a content of 75D hardness resin of about 50% or less were below 45°. The 20% 75D hardness resin tubing actually exhibited the lowest residual angle, which fell short of full recovery to the straight tube configuration by only 21°.

Test lengths of tubing manufactured from duplicate samples of the extrudate samples reported in TABLE 2A were tested for volumetric flow rate under 90 degree bend conditions. First, the test lengths were disposed in an approximately straight path between known inlet and outlet hydraulic conditions and volumetric flow rates were measured. Secondly, the test lengths were forced into 90 degree bends and volumetric flow rates were measured again, using the same inlet and outlet hydraulic conditions. The results of the 90 degree bend flow testing are presented in FIG. 2B.

Test lengths of tubing manufactured from the duplicate samples were also tested for residual angle upon release from a 90 degree bend condition. Straight lengths which had not experienced previous bending were selected. Each of the duplicate samples was folded into a 90 degree bend, held motionless for a predetermined period of time, and released. The residual angle, expressed as the number of degrees which each released length of tubing fell short of returning to a straight angle, are recorded on the right-hand axis of FIG. 2B.

Figure 2B:
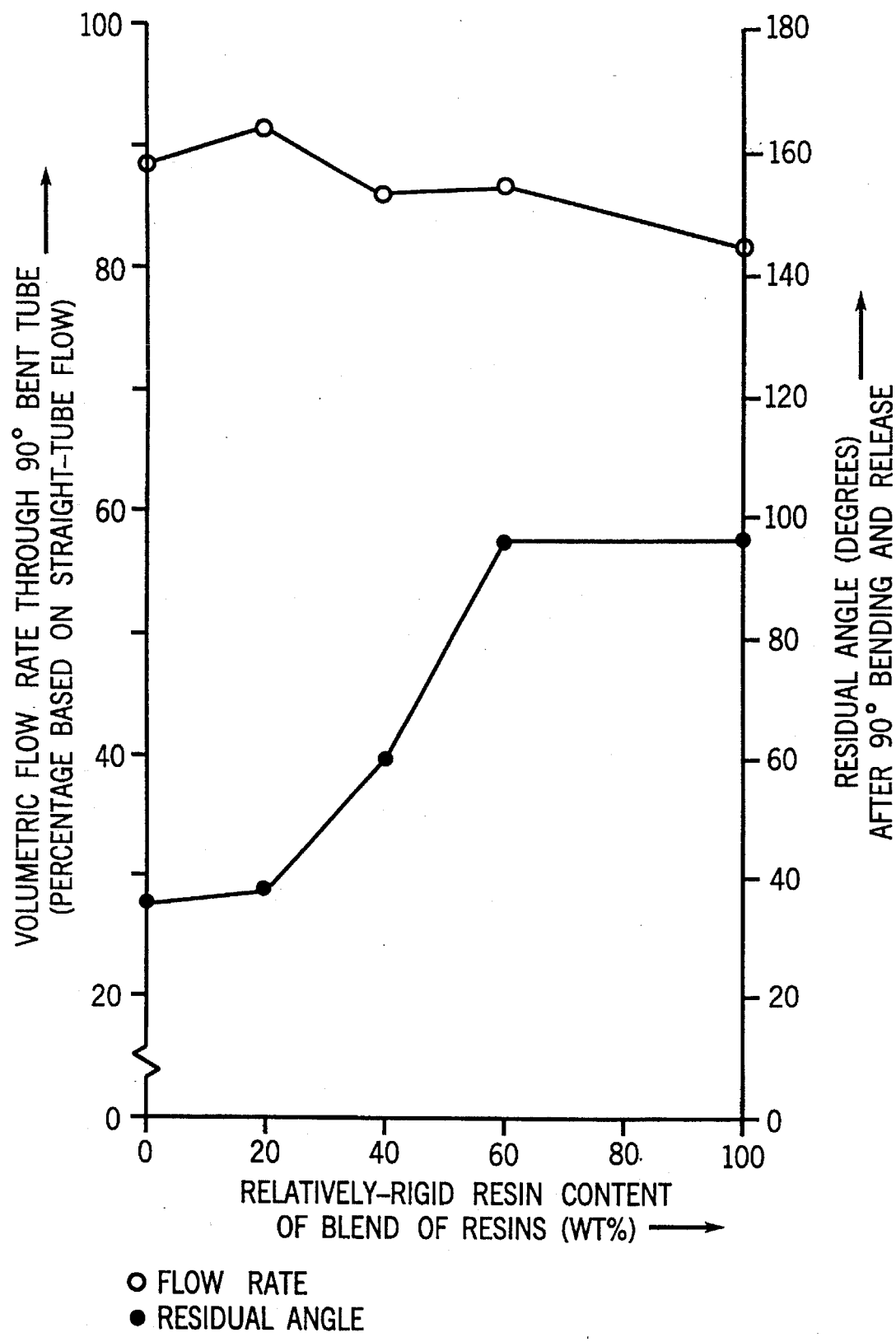
FIG. 2B illustrates change in volumetric flow rate (through tubing bent 90 degrees) and residual angle (after 90 degree bend) of tubing made from polyurethane compositions as the percentage of relatively rigid resin varies.

The data in FIGS. 1, 2A, and 2B demonstrate that tubing containing from about 20% to about 50% of a resin exhibiting 75D hardness, with the balance being 65D hardness resin, has surprisingly useful properties. Tubing with more than about 50% of the relatively rigid resin is deficient in ultimate elongation, suffers a loss of volumetric capacity when folded, and displays a relatively high residual angle.

The invention also provides a method for injecting a therapeutic fluid into a human body. In this context, a therapeutic fluid may be, for example, an anesthetic, an anti-microbial agent, or a diagnostic fluid. Further, the method for injecting fluid is readily adaptable for withdrawing a body fluid as, for example, to obtain fluid samples for laboratory analysis.

The method for injecting a therapeutic fluid comprises providing a tube member formed of a blend of resins. Most often the tube member will have an outside diameter in the range of about 0.010 of an inch to about 0.060 of an inch. About 0.015 of an inch outside diameter is preferred for injections into the cerebrospinal fluid. The thickness of the tubing wall is preferably in the range of about 0.004 to about 0.008 of an inch. The tube member is preferably smooth on both its inner and outer surfaces and must be reasonably biocompatible for the period during which therapeutic fluid is injected.

The tube member is formed of a blend of resins having a tensile strength of about more than 7000 psi, and possibly 10,000 psi. The specified degree of tensile strength lessens the chance of the tube member breaking while it is being withdrawn or manipulated within a human body.

The tube member preferably exhibits an ultimate elongation of more than about 200% so that the tube member may conform with the structure of the organ or cavity into which it is inserted. It is especially preferred that the tube member exhibit an ultimate elongation of 300% or more. This degree of elongation tends to insure that the tube member will not be broken by a patient's normal body movement.

The necessary combination of tensile strength, ultimate elongate, and kink recovery is provided by a tube member which comprises from about 50% to about 80% by weight of an elastomeric polyurethane resin having a hardness in the range of about 60 to about 70 Shore D units. The elastomeric resin blended with about 20% to about 50% by weight of a relatively rigid polyurethane resin, having a hardness of about 10 Shore D units greater, produces a tube member having sufficient strength and hardness to penetrate into small, well-protected regions of the human body. Yet the blend is sufficiently strong and flexible to function without injuring the patient.

The method comprises passing the therapeutic fluid through the tube member and into the body. The flow of therapeutic fluid may be continuous or intermittent, as the particular medical application dictates. The flow may be controlled according to predetermined liquid volumes or volumetric flow rates, on the basis of fluid pressure within the body, or by reference to other clinical indications. The tube member may be withdrawn between injections, but preferably will be left in place throughout a term of treatment.

The invention also provides a method of manufacturing tubing. The method comprises mixing an elastomeric polyurethane resin with a relatively rigid polyurethane resin. The mixing may be accomplished between dry solids, as for example, between resin pellets having different physical and chemical properties. Alternatively, the mixing may be accomplished by the well known industrial hot melt process where different resins are brought together in a fused liquid state.

The elastomeric resin is present in an amount of from about 50% to about 80% by weight based on a blend of resins. The elastomeric resin has a hardness in the range of about 60 to 70 Shore D units. Also present in the mixture of resins is about 20% to about 50% by weight of the relatively rigid resin. The hardness of the relatively rigid resin exceeds that of the elastomeric resin by about 10 Shore D units. The mixing produces a mixture of resins which may include other desirable components such as a stabilizing agents or radialopaque compounds.

Fusing the mixture of resins produces a blend of resins having a tensile strength, an ultimate elongation, and a hardness suitable for tubing which may be used as a catheter. The blend of resins has a tensile strength of more than 7000 psi, preferably more than 10,000 psi. The blend exhibits an ultimate elongation of greater than about 100%, preferably greater than about 300%. The blend of resins is extruded to produce the tubing.

The method of manufacturing described above is further characterized in some aspects of the present invention in that the extruding is done through a tubing die having an average diameter which is in the range of about two to about ten times as large as the average diameter of the final tubing as measured after extrusion and, if necessary, cooling. "Draw diameter ratio" is defined as ratio of the two aforesaid diameters. It is especially preferred that the tubing be extruded from a die which has a draw diameter ratio of about 4.0.

It has been discovered that the relative dimensions of the tubing die during extrusion significantly effect physical properties of the finished tubing. In particular, tensile strength and ultimate elongation increased when certain ranges of diameter draw ratio and wall draw ratio were utilized during the extrusion. "Wall draw ratio" is defined as a die gap through which a tubing wall issues during extrusion divided by a final tube wall thickness after extrusion and, if necessary, cooling. Best results were obtained using a wall draw ratio of about 4.0. The following example demonstrates the effect of diameter draw ratio on physical properties of the tubing.

EXAMPLE 3

Four samples of resin were prepared. Each comprised 50% by weight of a 65D hardness thermoplastic urethane resin and 50% by weight of a 75 Shore D hardness thermoplastic polyurethane resin. Two of these mixtures were prepared by dry mixing and two were melt-blended.

All four Samples were. Subsequently extruded to produce tubing. The two dry mixed samples and one of the melt-blended samples were extruded through a tubing die having a draw diameter ratio of 6.0 to 1.0. One melt-blended mixture of resins was extruded at a draw diameter ratio of 10.0 to 1.0. In every case, the tubing so manufactured, was tested for tensile strength and ultimate elongation. The results of the testing are disclosed in TABLE 3.

TABLE 3

| | Effect Of Extrusion Conditions On Finished Tubing Properties | | |
| --- | --- | --- | --- |
| | Draw Diameter Ratio (dimensionless) | Ultimate Tensile Strength (psi) | Ultimate Elongation (%) |
| Dry mixed | 6.0:1.0 | 7350 | 115 |
| Dry Mixed (retest) | 6.0:1.0 | 7630 | 126 |
| Melt blended | 6.0:1.0 | 8700 | 182 |
| Melt blended | 10.0:1.0 | 9460 | 205 |

The test results indicate that all of the mixtures formed tubing having physical properties suitable for medical tubing. All of the tensile strengths measured were over 7000 psi. The ultimate elongations were over 100%.

The two dry mixed samples were manufactured and tested at the same conditions, one being a retest of the other. Together, they provide an indication of the reproducibility of the manufacturing and testing methods.

samples were prepared by the melt blending procedure

The nine samples were extruded to produce tubing. Physical properties of the tubing produced as well as some details of the extrusion conditions are set forth in TABLE 4.

TABLE 4

| | Extruded Sample No. | | | | | | | | |
|---|---|---|---|---|---|---|---|---|---|
| | 1 | 2 | 3 | 4 | 5 | 6 | 7 | 8 | 9 |
| Extrusion Conditions: | | | | | | | | | |
| Diameter Draw Ratio | 4.16 | 3.80 | 4.11 | 4.34 | 3.18 | 3.39 | 3.22 | 4.24 | 4.05 |
| Wall Draw Ratio | 5.23 | 5.00 | 3.86 | 4.15 | 3.66 | 5.57 | 5.00 | 4.53 | 4.66 |
| Area Draw Ratio | 21.8 | 19.0 | 15.6 | 18.0 | 11.6 | 18.9 | 16.1 | 19.2 | 18.9 |
| Physical Properties: | | | | | | | | | |
| Modulus | 26,360 | 22,800 | 24,430 | 27,570 | 18,770 | 23,780 | 19,860 | 20,640 | 24,630 |
| Yield Strength (psi) | 11,330 | 9,300 | 6,290 | 9,955 | 8,640 | 9,430 | 8,320 | 9,300 | 9,275 |
| Yield Elongation (%) | 430 | 410 | 274 | 466 | 450 | 380 | 360 | 395 | 360 |
| Ultimate Strength (psi) | 11,330 | 9,300 | 6,290 | 9,955 | 8,640 | 9,430 | 8,320 | 9,300 | 10,650 |
| Ultimate Elongation (%) | 430 | 410 | 274 | 466 | 450 | 380 | 360 | 395 | 430 |

A primary difference between the tubing which tested with an ultimate tensile strength of 7630 psi and the tubing which tested with an ultimate tensile strength of 8700 psi is that the latter was melt-blended, rather than dry mixed. The data indicates that melt-blending leads to a product having superior tensile strength and ultimate elongation properties, possibly resulting from more intimate contact between the two resins.

Best results were obtained by melt-blending the two resins in equal proportions and then extruding the resulting blend through a tubing die having a draw diameter ratio of 10.0 to 1.0. From TABLE 3, it is apparent that both the draw diameter ratio and the method of mixing the resins affects the physical properties of the final tubing. The data in TABLE 3 indicate that it is preferable to melt-blend and employ a draw diameter ratio of about 10.0 to 1.0.

Surprisingly, high tensile strength and elongation were observed consistently in tubing extruded at area draw ratios greater than approximately 18 to 1. Area draw ratio is the ratio of the cross-sectional area of a portion of a tubing die through which extruded material will issue divided by the cross-sectional area of a final tube wall after extrusion and, if necessary, cooling. The area draw ratio may be conveniently calculated by multiplying the wall draw ratio times the diameter draw ratio. The following example demonstrates the effect of diameter draw ratio, wall draw ratio, and area draw ratio on physical properties of the tubing.

EXAMPLE 4

Nine samples of resin were prepared Each comprised 75% by weight of a 65 D hardness thermoplastic polyurethane resin, and 25% by weight of a 75 Shore D hardness thermoplastic polyurethane resin Each sample also contained 20% by weight of barium sulfate ($BaSO_4$). All of the The data in TABLE 4 indicates that the most desirable combination of high yield strengths and high elongation are obtained when the diameter draw ratio and the wall draw ratio are simultaneously greater than 4. Generally, area draw ratios of 18 or more produced the best results.

The method of manufacturing tubing provided by the present invention may optionally include the step of cooling the blend after it has been fused in order to produce a solid intermediate product. Such an intermediate project may be stored for long periods without deterioration and is easily transported to another location for further processing.

The invention provides a method of manufacturing tubing which comprises injection molding a blend of resins to produce short tube sections. The method comprises mixing an elastomeric polyurethane with a relatively rigid polyurethane resin as described above in regard to the method of manufacturing tubing by extruding. The mixture of resins so produced is fused and then injection molded.

In accordance with the preceding discussion, further adaptations and variations of the present invention will be readily perceived by those of ordinary skill in the art. Therefore, the present invention should be interpreted in accordance with the language of the following claims and not solely in accordance with the particular embodiments of the invention that are described herein.

What is claimed is:

1. Tubing, suitable for use as a catheter which continues to deliver flow when tightly folded, formed of a composition which comprises a blend of resins having a tensile strength of more than about 7000 psi and an ultimate elongation of greater than about 100%, said blend comprising from about 50% to about 80% by weight of an elastomeric polyurethane resin having a hardness in the range of about 60 to about 70 Shore D units and from about 20% to 50% by weight of a relatively rigid polyurethane resin having a hardness of about 10 Shore D units greater than the hardness of the elastomeric resin.

2. The tubing of claim 1, further characterized in that the elastomeric resin has an ultimate elongation of more than about 100% and the relatively rigid resin has an ultimate elongation of less than about 50%.

3. The tubing of claim 1, further characterized in that the blend of resins is a thermoplastic elastomer.

4. The tubing of claim 1, further characterized in that the tubing has a passage for flow within and exhibits a residual angle of about 45 degrees or less after being folded in a tight 180 degree bend, pinched until the passage for flow is blocked, and released.

5. The tubing of claim 4, further characterized in that the tubing, when folded into a tight 90 degree bend, is capable of passing about 85% or more of the flow that could be passed by a straight tube of equal dimensions.

6. A method of manufacturing tubing suitable for use as a catheter, which comprises:

mixing from about 50% to about 80% by weight of an elastomeric polyurethane resin having a hardness in the range of about 60 to about 70 Shore D units with from about 20% to about 50% by weight of a relatively rigid polyurethane resin having a hardness of about 10 Shore D units greater than the hardness of the elastomeric resin to produce a mixture of resins;

fusing the mixture of resins to produce a blend of resins having a tensile strength of more than about 7000 psi and an ultimate elongation of greater than about 200%; and extruding the blend of resins to produce the tubing.

7. The method of claim 6, further characterized in that the elastomeric resin has an ultimate elongation of more than about 100% and the relatively rigid resin has an ultimate elongation of less than about 50%.

8. The method of claim 6, further characterized in that the blend of resins is extruded from a die having an average diameter which is in the range of about 2.0 to about 10.0 times as large as the average diameter of the tubing after said extruding.

9. The method of claim 8, further characterized in that the blend of resins is extruded from a die having an average diameter which is in the range of about 4.0 to about 5.0 times the average diameter of the tubing after said extruding.

10. The method of claim 6, further characterized in that the blend of resins is extruded from a die having a wall gap which is in the range of about 2.0 to about 10.0 times the wall thickness of the tubing after said extruding.

11. The method of claim 6, further characterized in that the blend of resin is extruded from a die having a diameter draw ratio of 4.0 to 10.0 and a wall draw ratio of 4.0 to 10.0.

12. The method of claim 6, further characterized in that the blend of resins is extruded from a die having an area draw ratio of 18.0 or more.

13. The method of claim 6, further characterized by cooling the blend of resins after said fusing to produce a solid intermediate product.

14. A method of manufacturing short tube sections, which comprises:

mixing from about 50% to about 80% by weight of an elastomeric polyurethane resin having a hardness in the range of about 60 to about 70 Shore D units with from about 20% to about 50% by weight of a relatively rigid polyurethane resin having a hardness of about 10 Shore D units greater than the hardness of the elastomer resin to produce a mixture of resins;

fusing the mixture of resins to produce a blend of resins having a tensile strength of more than about 7000 psi and an ultimate elongation of greater than about 200%; and injection molding the blend of resins to produce a short tube section.

* * * * *